US009682168B2

(12) United States Patent
Joshi et al.

(10) Patent No.: US 9,682,168 B2
(45) Date of Patent: Jun. 20, 2017

(54) D, L-CYCLIC PEPTIDE NANOTUBE REINFORCING AGENTS

(71) Applicant: President and Fellows of Harvard College, Cambridge, MA (US)

(72) Inventors: Neel Satish Joshi, Somerville, MA (US); Daniel James Rubin, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 14/360,851

(22) PCT Filed: Nov. 26, 2012

(86) PCT No.: PCT/US2012/066549
§ 371 (c)(1),
(2) Date: May 27, 2014

(87) PCT Pub. No.: WO2013/122642
PCT Pub. Date: Aug. 22, 2013

(65) Prior Publication Data
US 2014/0369954 A1 Dec. 18, 2014

Related U.S. Application Data

(60) Provisional application No. 61/563,894, filed on Nov. 28, 2011.

(51) Int. Cl.
| A61K 38/00 | (2006.01) |
| A61L 27/22 | (2006.01) |
| A61K 9/00 | (2006.01) |
| A61K 47/42 | (2017.01) |
| A61L 27/44 | (2006.01) |
| A61L 31/12 | (2006.01) |
| A61L 27/18 | (2006.01) |
| C08L 89/00 | (2006.01) |
| C08L 1/02 | (2006.01) |
| C08L 5/04 | (2006.01) |
| C08L 5/08 | (2006.01) |
| C08K 7/22 | (2006.01) |
| A61L 27/26 | (2006.01) |
| D01D 5/00 | (2006.01) |

(Continued)

(52) U.S. Cl.
CPC .......... *A61L 27/227* (2013.01); *A61K 9/0092* (2013.01); *A61K 47/42* (2013.01); *A61L 27/18* (2013.01); *A61L 27/26* (2013.01); *A61L 27/44* (2013.01); *A61L 31/125* (2013.01); *A61L 31/129* (2013.01); *C08K 7/22* (2013.01); *C08L 1/02* (2013.01); *C08L 5/04* (2013.01); *C08L 5/08* (2013.01); *C08L 89/00* (2013.01); *D01D 5/0053* (2013.01); *A61L 2400/12* (2013.01); *A61L 2430/02* (2013.01); *A61L 2430/10* (2013.01); *A61L 2430/34* (2013.01); *A61L 2430/38* (2013.01); *B82Y 30/00* (2013.01); *B82Y 40/00* (2013.01); *C08K 2201/011* (2013.01); *D10B 2331/041* (2013.01); *Y10T 428/249921* (2015.04)

(58) Field of Classification Search
None
See application file for complete search history.

(56) References Cited

U.S. PATENT DOCUMENTS

2007/0207182 A1* 9/2007 Weber et al. .................. 424/423
2010/0046345 A1* 2/2010 Fujita et al. .................. 369/100
(Continued)

FOREIGN PATENT DOCUMENTS

WO  WO-2013122642 A2  8/2013
WO  WO-2013122642 A3  8/2013

OTHER PUBLICATIONS

Ghadiri et al. Nature, vol. 366, Nov. 25, 1993.*
"International Application Serial No. PCT/US2012/066549, International Preliminary Report on Patentability mailed Jun. 12, 2014", 8 pgs.
Engels, Tom A. P., et al., "Time-dependent failure of amorphous polylactides in static loading conditions", *J. Mater. Sci. Mater. Med.*, 21(1), (2010), 89-97.
Han, Lin, et al., "Geometrically controlled mechanically responsive polyelectrolyte tube arrays", *Adv. Mater.*, 23(40), (2011), 4667-4673.
Smit, T. H., et al., "Time-dependent failure in load-bearing polymers: a potential hazard in structural applications of polylactides", *J. Mater. Sci. Mater. Med.*, 21(3), (2009), 871-878.
"International Application Serial No. PCT/US2012/066549, International Search Report mailed Sep. 23, 2013", 3 pgs.
(Continued)

Primary Examiner — Jeanette Lieb
(74) Attorney, Agent, or Firm — McCarter & English, LLP; Maria Laccotripe Zacharakis; Marcie B. Clarke

(57) ABSTRACT

The disclosed subject matter can provide a nanotube-reinforced polymer composite material comprising a plurality of nanotubes, each nanotube being formed of a plurality of cyclic peptide molecules, disposed within a polymer matrix, such as a biodegradable polymer matrix. A cyclic polymer, such as a cyclic 8-mer, composed of amino acid residues of alternating absolute configurations (D/L, R/S), can self-assemble into nanotubes useful for preparation of the composite polymer material of the invention. For example, the cyclic peptide (QL)4, wherein the glutamine and leucine residues are of opposite absolute configuration, self-assembles into nanotubes, which when formed into a reinforced polymer composite including poly(caprolactone), provides a biocompatible material of greater tensile strength and Young's modulus compared to the poly(caprolactone) material alone. The nanotubes can be prepared by a vapor equilibration technique or by a solvent-nonsolvent precipitation technique. The materials of the invention can be used for implants, stents and the like as well as for synthetic ligaments, tendons, cartilage, and bone for use in the living tissue of a patient in need thereof. For example, a spinal fusion cage comprising a PDLLA polymer matrix with a plurality of nanotubes of the invention can exhibit enhanced stiffness.

23 Claims, 16 Drawing Sheets

(51) Int. Cl.
*B82Y 30/00* (2011.01)
*B82Y 40/00* (2011.01)

(56) References Cited

U.S. PATENT DOCUMENTS

2010/0075904 A1* 3/2010 Laurencin et al. ............. 514/12
2011/0046345 A1* 2/2011 Kulp et al. ................... 530/317

OTHER PUBLICATIONS

"International Application Serial No. PCT/US2012/066549, Written Opinion mailed Sep. 23, 2013", 6 pgs.
Coleman, J. N., et al., "Small but strong: A review of the mechanical properties of carbon nanotube-polymer composites", Carbon, 44, (2006), 1624-1652.
Hartgerink, Jeffrey D., et al., "Self Assembling Peptide Nanotubes", J. Am. Chem. Soc., 118(1), (1996), 43-50.
Peng, F., et al., "Hydroxyapatite Needle-Shaped Particles/Poly(l-lactic acid) Electrospun Scaffolds with Perfect Particle-along-Nanofiber Orientation and Significantly Enhanced Mechanical Properties", J. Phys. Chem. C, 115(32), (2011), 15743-15751.
Yang, Peter J, et al., "Engineering Orthopedic Tissue Interfaces", Tissue Engineering Part B: Reviews, 15(2), (Jun. 2009), 127-141.
Hartgerink et al., "Self-Assembling Peptide Nanotubes", Journal of American Chemical Society, No. 118, pp. 43-50 (1996).

\* cited by examiner

----- PCL
——— PCL + 11% QL4-NT
■■■ PCL/GEL
— — PCL/GEL + 11% QL4-NT

D, L-CYCLIC PEPTIDE NANOTUBE REINFORCING AGENTS

CROSS-REFERENCE TO RELATED APPLICATIONS

This application is a U.S. National Stage Application under 35 U.S.C. 371 of PCT/US2012/066549, filed Nov. 26, 2012, and published on Aug. 22, 2013 as WO 2013/122642 A2, which claims the priority of U.S. provisional patent application Ser. No. 61/563,894, filed Nov. 28, 2011, the disclosure of which are incorporated herein by reference in their entirety.

STATEMENT OF GOVERNMENT SUPPORT

This invention was made with government support under DMR-0820484 awarded by National Science Foundation, and W911NF-12-1-0229 and ARO 167836, awarded by United States Army Research Office. The government has certain rights in the invention.

BACKGROUND

Nanoscale composites have been composed from a variety of components including hydroxyapatite nanoparticles (see Peng, F; Shaw, M; Olson, J; *J. Phys. Chem.* 115, 15743-15751 (2011)) for bone engineering and carbon nanotubes for performance composite fibers (see Coleman, J. N; Khan, U; Blau, W. J; Gun'ko Y. K *Carbon* 44, 1624-1652 (2006). Within the biomedical field, the major existing technology for synthetic biocompatible materials is based on combinations of poly(lactic acid), poly(glycolic acid) and poly(caprolactone) (see Yang, P. J; Temenoff, J. S *Tiss Eng. Pt B,* 15 127-141 (2009). These materials are currently FDA approved for a variety of applications, however they suffer from acidic decomposition products and fixed degradation rates. In some cases, including vascular stents, they also lack the mechanical rigidity necessary to function.

DLCPs themselves were synthesized in the mid 1990s by Dr. Reza Ghadiri at the Scripps Research Institute; see Hartgerink, J; Granja, J; Milligan, R; Ghadiri, M, *J. Am. Chem. Soc* 118, 43-50 (1996).

SUMMARY

In various embodiments, the invention is directed to DLCP nanotube reinforced polymer composites, comprising D,L-cyclic peptide (DLCP) nanotubes disposed within samples of biocompatible polymers, the DLCP nanotube reinforced polymer composite materials having improved properties over prior art materials; to synthetic biostructures such as implants and synthetic body tissues comprising the DLCP nanotube reinforced biocompatible polymer composite materials; to methods of making the DLCP nanotube composite materials and methods of fabricating the synthetic biostructures comprising the materials; and to methods of using the DLCP nanotube reinforced composite materials and methods of using the synthetic biostructures prepared comprising the DLCP nanotube reinforced composite materials. By incorporating DLCP nanotubes (DLCP-NT) into biocompatible polymer materials, such as poly(caprolactone) and poly(caprolactone)/gelatin blends, the ability of DLCP nanotubes to mechanically reinforce the polymeric materials and provide polymer composites of exceptional properties, was discovered by the inventors herein.

In a basic and novel form, a composite material of the disclosed subject matter is a nanotube-reinforced polymer composite material, wherein a plurality of nanotubes, each nanotube comprising a plurality of individual molecules of a D,L cyclic peptide (DLCP), is disposed within a biocompatible polymer. The DLCP can be formed of alternating D and L α-amino acid units within each cyclic peptide unit, e.g., an 8-mer cyclic form of two alternating amino acid types, the two types having opposite absolute configurations. The biocompatible polymer can be, e.g., poly(caprolactone), a poly(caprolactone)/gelatin blend, a poly(lactide), a poly(glycolide), or a poly(lactide-glycolide), a poly-D,L-lactic acid (PDLLA), or any other biocompatible organic polymer suitable for a particular use in tissue engineering and repair.

In various embodiments, the invention can provide a method of producing the DLCP nanotube reinforced biocompatible polymer composite material of the invention, including fibers prepared by methods including electrospinning. Fibers of the DLCP nanotube reinforced biocompatible polymer composite can be formed into fibrous meshes, both random and aligned In various embodiments, the invention can provide a synthetic biostructure, such as a stent, a suture, a wound dressing, or a synthetic ligament, tendon, cartilage, or bone material, adapted for emplacement within living tissue of a patient, comprising a DLCP nanotube reinforced biocompatible polymer composite material of the invention, or prepared by a method of the invention. For example, the DLCP nanotube reinforced biocompatible polymer composite can be used to increase the stiffness of medical devices for implantation, such as spinal fusion devices, e.g., spinal fusion devices formed at least in part of PDLLA.

DETAILED DESCRIPTION

Definitions

Figure 1A:
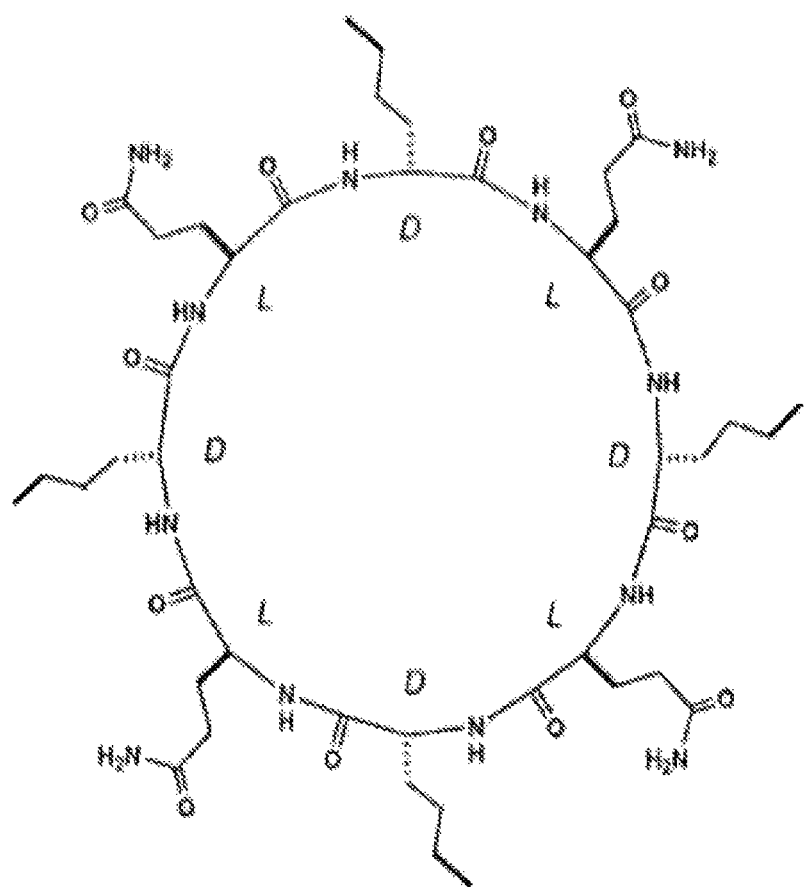
FIG. 1: (A) Chemical structure of DLCP $(QL)_4$. (B) Morphology of $(QL)_4$ nanotubes used for mechanical reinforcement. Crystal dimensions are ~75 um in length, and ~300 nm in height and width. The nanotubes were prepared using the trifluoracetic acid-water precipitation method described in the Examples, below.

A "nanotube" as the term is used herein refers to an elongate molecular assembly of multiple cyclic peptide molecules, which can be approximately cylindrical, or bent cylindrical, in physical form, having a diameter on the scale of about a nanometer (nm), with length varying up to a micron (μm) or greater.

A D,L cyclic peptide (DLCP), such as can form a nanotube, is a cyclic peptide of about 6-12 α-amino acid residues. Each molecule of the DLCP is composed of at least two different amino acid types, in alternation with each other in the structure of the cyclic peptide. Each molecule of the DLCP may be composed of any combination of amino acids with natural or unnatural side chains, provided the amino acids are α-amino acids and provided the α-amino acids bear one α-hydrogen atom. The absolute stereochemistry of the amino acid residues forming the DLCP alternate sequentially, such that the cyclic peptide can assume an approximately circular conformation with the amino acid sidechain residues projecting to the exterior of the circle. In this conformation, the cyclic peptide molecules can self assemble in an energetically favorable process to form an approximately cylindrical supramolecular nanotube that is stable on forming to withstand temperatures at least as great at body temperature (37° C.).

D- and L-forms of amino acid residues as forming the cyclic peptides that can self-assemble into the DLCP nanotubes used in the polymer composite material of the invention are equivalent to the R and S forms of the amino acids, as defined using the CIP rules as discussed below. The isomers resulting from the presence of a chiral center comprise a pair of non-superimposable isomers that are called "enantiomers." Single enantiomers of a pure compound are optically active, i.e., they are capable of rotating the plane of plane polarized light. Single enantiomers are designated according to the Cahn-Ingold-Prelog (CIP) system. Once the priority ranking of the four groups is determined, the molecule is oriented so that the lowest ranking group is pointed away from the viewer. Then, if the descending rank order of the other groups proceeds clockwise, the molecule is designated (R) and if the descending rank of the other groups proceeds counterclockwise, the molecule is designated (S). In the example in Scheme 14, the Cahn-Ingold-Prelog ranking is A>B>C>D. The lowest ranking atom, D is oriented away from the viewer.

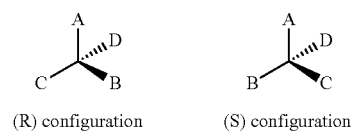

(R) configuration     (S) configuration

For example, L-leucine can also be termed S-leucine, and D-leucine can also be termed R-leucine. The relationship between the D/L designation and the R/S designation for amino acids is well known in the art.

A "cyclic peptide" as the term is used herein refers to a molecular entity formed of α-amino acid residues bonded via α-amide bonds, wherein a C-terminus and an N-terminus of the peptide are themselves bonded to each other to form a ring. A cyclic peptide such as used herein for formation of nanotubes can have from about 6 to about 12 α-amino acid residues. A "D,L cyclic peptide" as the term is used herein refers to a cyclic peptide wherein the amino acid residues alternate in absolute configuration progressing around the ring. Thus, a D,L cyclic peptide, for example a cyclic 8-mer (having 8 amino acid residues per cyclic molecule), has a structure that can be depicted as

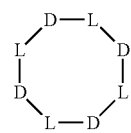

or, more generally, as

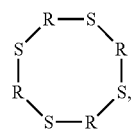

wherein the D and L refer to the absolute configuration of the amino acid (as it relates to the absolute configuration of D and L glutaraldehyde), and the R and the S refer to the absolute configuration of each amino acid as determined by the CIP absolute configuration rules described above and within knowledge of the ordinary practitioner. A "cyclic peptide" within the meaning herein is formed of α-amino-acids bearing an α-hydrogen atom and a second α-substituent. It is the chirality of this α-center to which the D/L or R/S designations refer.

A "polymer matrix" as the term is used herein refers to an organic polymer in which the DLCP nanotubes can be embedded, optionally physically oriented with each other, to provide a DLCP nanotube reinforced polymer composite of the invention. A "biocompatible" polymer is a polymer of a type that can be used in contact with living tissue, as in a human patient", without causing serious damage or deterioration of the living tissue with which it is in contact. Examples include poly(caprolactone) (PCL) and poly(lactide-glycolide) (PLG), such as are well known in the art. A polymer matrix can comprises a synthetic polymer, like poly(caprolactone), a poly(caprolactone)/gelatin blend, a poly(lactide), a poly(glycolide), or a poly(lactide-glycolide), or a naturally occurring biopolymer, like chitosan, hyaluronic acid, cellulose, alginate, or silk.

A "polymer composite" as the term is used herein refers to a DLCP nanotube reinforced polymer matrix, i.e., a fiber-reinforced polymer sample wherein the "fiber" includes at least the DLCP nanotubes, and, optionally, additional fiber reinforcement components. When the polymer composite is to be formed into a linear structure such as a synthetic tendon, the "fibers", i.e., the DLCP nanotubes, can be oriented accordingly, such as along a single axis, such as by use of spinning and drawing or other fiber orientation techniques, to provide anisotropic materials.

A "synthetic biostructure" as the term is used herein refers to a polymer composite comprising the DLCP nanotubes that has been formed into or incorporated into an object of defined design adapted to be used in treatment or repair of living tissues in a patient in need thereof. Examples include a stent, a suture, a wound dressing, or a synthetic ligament, tendon, cartilage, or bone material. A synthetic biostructure can be, for example, a shaped piece for filling a damaged portion of a bone, or aiding in the connection of a torn ligament to a bond or muscle, or repairing torn cartilage as in a bone joint, and the like. In various embodiments, a synthetic biostructure can be a shaped object for reconstructive surgery such as an interior portion of an ear or a nose. In other embodiments a synthetic structure can be an adhesive layer connecting body parts such as bone and ligament, and the like.

DETAILED DESCRIPTION

Figure 1B:
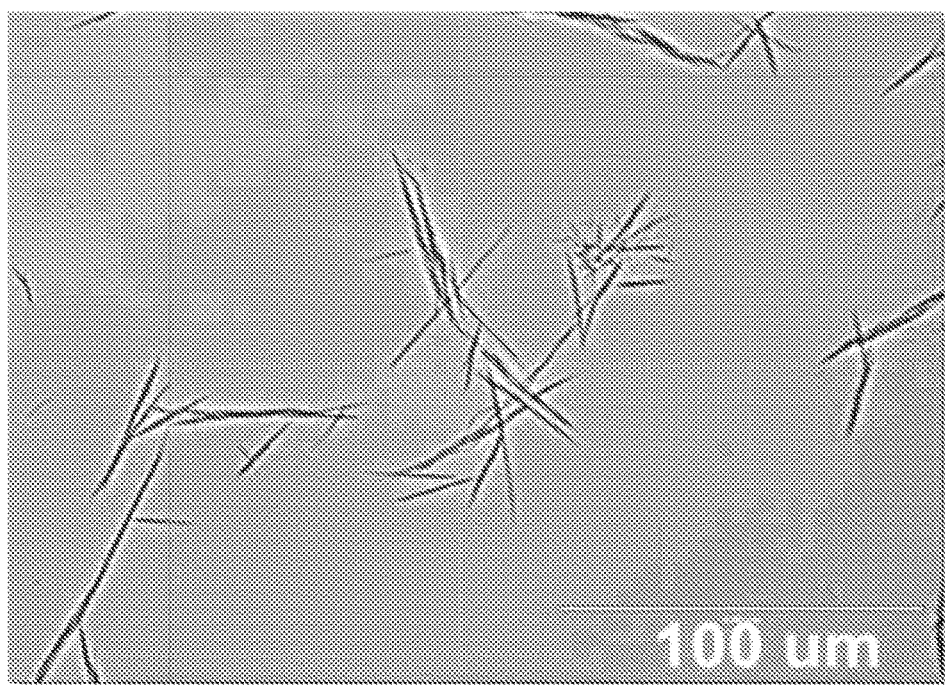
Figure 2A:
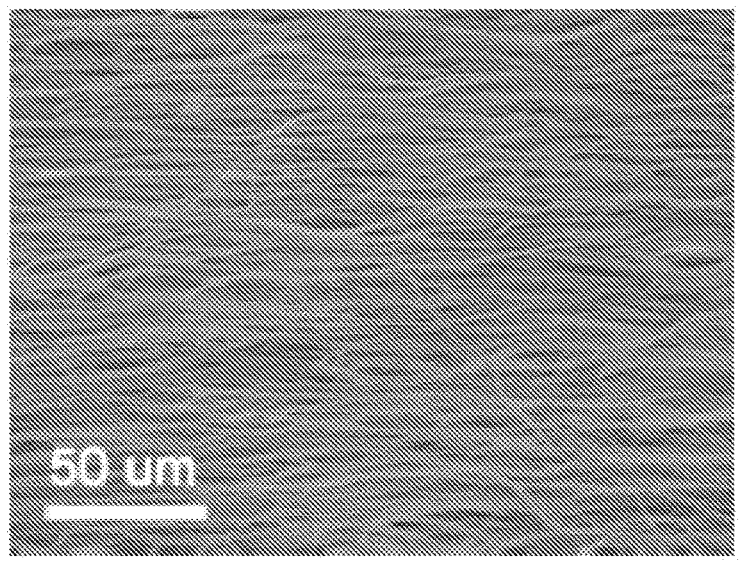
FIG. 2: (A) Scanning electron micrograph of a nanofiber mesh composed of PCL containing $(QL)_4$ nanotubes. (B) Transmission electron microscopy of embedded $(QL)_4$ crystals within PCL nanofibers. (C) Fourier-transform infrared (FT-IR) spectroscopy displaying peaks characteristic of DLCP-NTs within the PCL fiber.
Figure 2B:
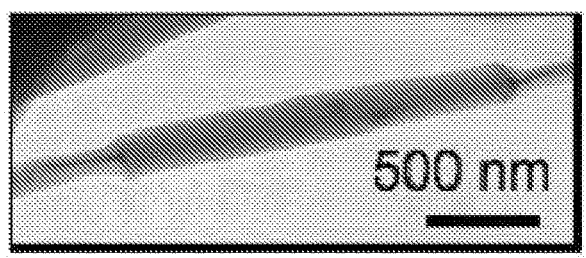
Figure 2B:
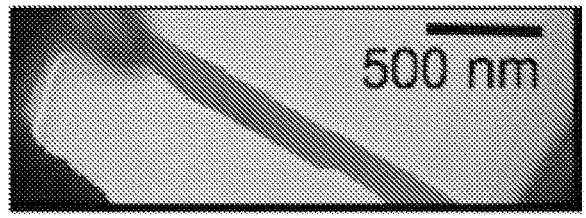
Figure 2C:
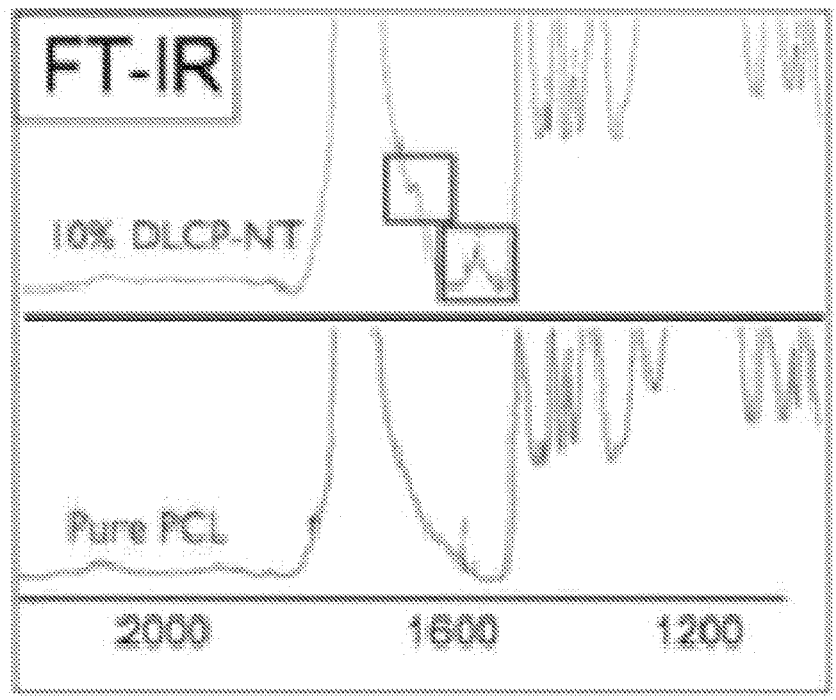

In various embodiments, a self-assembling peptide system comprising a D,L-cyclic peptide is used to mechanically reinforce poly(caprolactone) (PCL) and PCL/gelatin blends, commonly used tissue engineering polymers. DLCPs are composed of eight alternating D- and L-α-amino acids. Because of their alternating stereochemistry, the amino acid side chains radiate from the center of the ring and the amide backbone is oriented perpendicular to the ring face, allowing for tube formation via beta-sheet hydrogen bonding. Due to this structural geometry, the surface chemistry and assembly dynamics of DLCPs are uniquely independent, providing an interesting building block for composite material design. DLCP nanotubes (DLCP-NTs) composed of alternating glutamine (Q) and leucine (L) amino acids, $(QL)_4$ (FIG. 1), were co-spun with (PCL) and PCL/Gelatin blends, to create nanofiber meshes (FIG. 2) with improved ultimate tensile strength (UTS) and Young's modulus (FIG. 3).

DLCP nanotubes can be prepared, for example, by formation of the cyclic peptide in a solvent, followed by precipitation from the solvent (e.g., trifluoracetic acid) to which water is added. Nanotubes can be separated from the precipitation milieu by methods comprising centrifugation, filtration, and the like.

In various embodiments, the invention provides a nanotube-reinforced polymer composite, comprising a plurality of nanotubes within a polymer matrix, each nanotube comprising a self-assembling plurality of D,L cyclic peptide molecules, each D,L cyclic peptide molecule being a cyclic oligomer of about 6-12 α-amino acid residues, the amino acid residues of each cyclic peptide molecule having alternating absolute configurations. As each amino acid residue bears on α-hydrogen and one non-hydrogen substituent, the bulky non-hydrogen substituent projects outwardly from the surface of the assembled nanotube. The nanotubes can be aligned with each other within the polymer matrix, such as in a fiber or a ribbon, to give the material an anisotropy, such as for a synthetic tendon or ligament, when stress is exerted along a longitudinal axis to a greater extent than along a transverse axis.

In various embodiments, such as for preparation of polymer composites of the invention for use in tissue repair and in contact with living tissue, the matrix of polymeric material can comprise one or more biocompatible polymer. For example, the polymer matrix can comprise a synthetic polymer, like poly(caprolactone), a poly(caprolactone)/gelatin blend, a poly(lactide), a poly(glycolide), or a poly(lactide-glycolide), or a naturally occurring biopolymer, like chitosan, hyaluronic acid, cellulose, alginate, or silk. In various embodiments, the amino acid residues making up the cyclic peptide oligomer can have alternating absolute configurations such that one type of amino acid is of a first absolute configuration, and a second type of amino acid is of an opposite absolute configuration. More specifically, the first type of amino acid can be glutamine and the second type can be leucine, wherein the glutamine and the leucine are of opposite absolute configuration; or the first type of amino acid can be glutamate and the second type can be alanine, wherein the glutamate and the alanine are of opposite absolute configuration. In various embodiments, the cyclic peptide is formed of only two types of amino acid, such as glutamine and leucine, or glutamate and alanine. By a "type" of amino acid is meant a three dimensional chemical structure of an amino acid, thus, D-alanine and L-alanine would be considered different amino acid "types" within the meaning herein. Thus, a cyclic peptide capable of forming a nanotube for inclusion in a polymer matrix to provide a polymer composite of the invention can be composed of alternating D-alanine and L-alanine, or alternating D and L (R and S) forms of a single amino acid residue having a chiral carbon atom.

Figure 4:
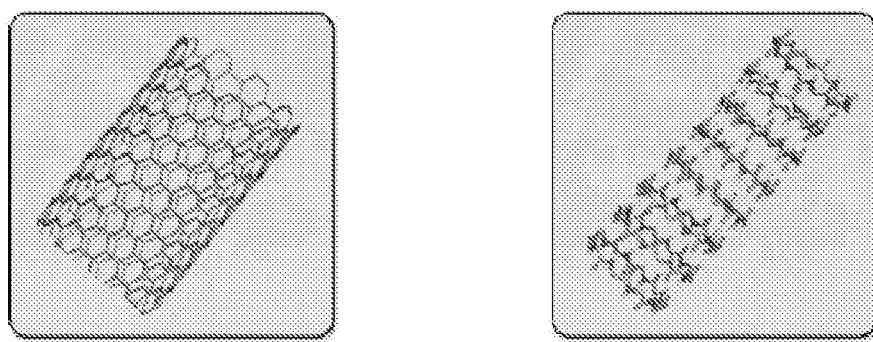
FIG. 4 provides a comparison of carbon nanotubes and DLCP nanotubes with respect to their applicability in reinforcement of polymeric materials.

Therefore, a DLCP must include at least two amino acid types, of opposite absolute configuration. The two amino acid types must alternate in sequence around the cyclic peptide. In this way, formation of a nanotube with the amino acid sidechains projecting outwardly is possible. The conformation wherein the peptide backbone can approximate a circular form, with the sidechains extending outwardly, is energetically achievable, such that multiple molecules of this structure can self-assemble into a nanotube such as is shown in FIG. 4.

In other embodiments, each cyclic peptide molecule can include more than two amino acid types. For example, the cyclic peptide can comprising a third type of amino acid, wherein the third type substitutes in the cyclic peptide for an amino acid residue of the same absolute configuration. An example is the cyclic polymer QKQAQAQA, which includes three types of amino acid residues, of alternating absolute configurations, and can form nanotubes suitable for use in polymer composites of the invention.

The amino acid sidechains, projecting outwardly from the exterior of nanotubes formed by self-assembly of the DLCP molecules, can be further functionalized to optimize interfacial interactions with the surrounding matrix. This further functionalization of DLCPs may occur before or after nanotube assembly and processing into a polymer composite. The functionalization may also result in enhanced covalent bonding or non-covalent interaction with the surrounding matrix in order to reinforce the inventive composite. For example, the sidechains can be made available for covalent crosslinking with a polymer matrix, such that the polymer composite can be physically stronger than a matrix wherein the nanotubes are only physically and non-covalently associated with the polymer matrix. For example, the sidechains can be made available such that the surface of a sample of the inventive polymer composite is suited for interaction with an exterior substrate, e.g., for interaction of a surface of a synthetic tendon with a point of attachment on bone, or on muscle, or the like, or to facilitate bonding of the inventive polymer composite when used as a bone adhesive and filler with surfaces of a fractured bone, or in similar applications wherein a synthetic tissue needs anchoring to another body tissue in carrying out a repair of damaged organs in a patient.

Figure 12B:
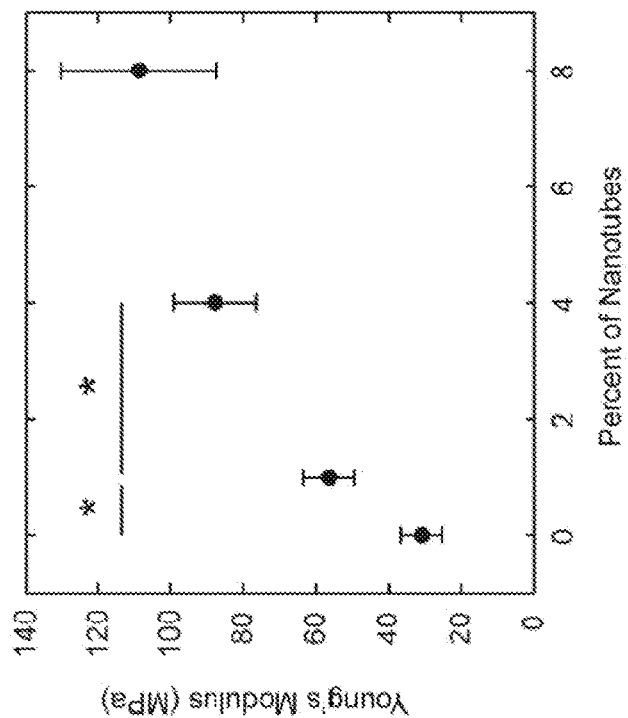
FIG. 12 shows (A) Force versus Displacement curves for indentation of composite fibers containing 0%, 1%, 4%, and 8% weight-to-weight percentage of (QL)$_4$ nanotubes. Error bars represent one standard deviation (n=16). (B) Young's Modulus versus weight percentage of (QL)$_4$ nanotube incorporation. Error bars represent one standard deviation (n=16).
Figure 12A:
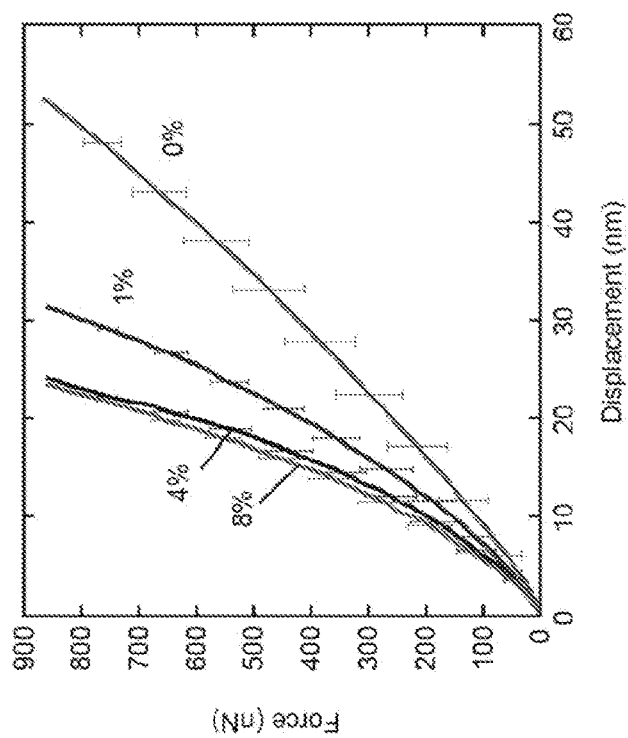

A specific example is shown herein, seen in FIG. 12, wherein a nanotube prepared with pendant exterior carboxylic acid groups is complexed with gold atoms by treatment of the functionalized nanotube with a gold salt in a reducing environment.

The polymer material in which the nanotubes are dispersed can be any suitable polymer; a biocompatible polymer is preferred if the material is to be used in a synthetic biostructure such as an implant, or will come in contact with living tissue of a patient. For example, the polymer material can comprise a poly(caprolactone), a poly(caprolactone)/gelatin blend, a poly(lactide), a poly(glycolide), or a poly (lactide-glycolide), or any combination thereof.

FIG. 4 shows graphically a comparison of art carbon nanotubes and DLCP nanotubes such as are used in various embodiments of the inventive polymer composite. DLCP nanotubes can be about 1 nm in diameter, and range from about 100 nm up to at least one micron in length, thus can be of comparable dimensions to single-walled carbon nanotubes. While both types of nanotubes are relatively stiff and provide high surface area, the DLCP nanotubes offer additional useful features, such as facile surface modification through elaboration of the amino acid sidechains that are disposed on the exterior surface of the nanotubes, and greater flexibility in diameter through variation of the cyclic peptides selected for formation of the nanotubes. In various embodiments, the cyclic peptides can be 8-mers of alternating D and L forms of α-amino acids, such as glutamine and leucine; or, in other embodiments, smaller or larger cyclic oligomers can be used, resulting in variation of the nanotube diameter and length/diameter ratio.

Figure 5:
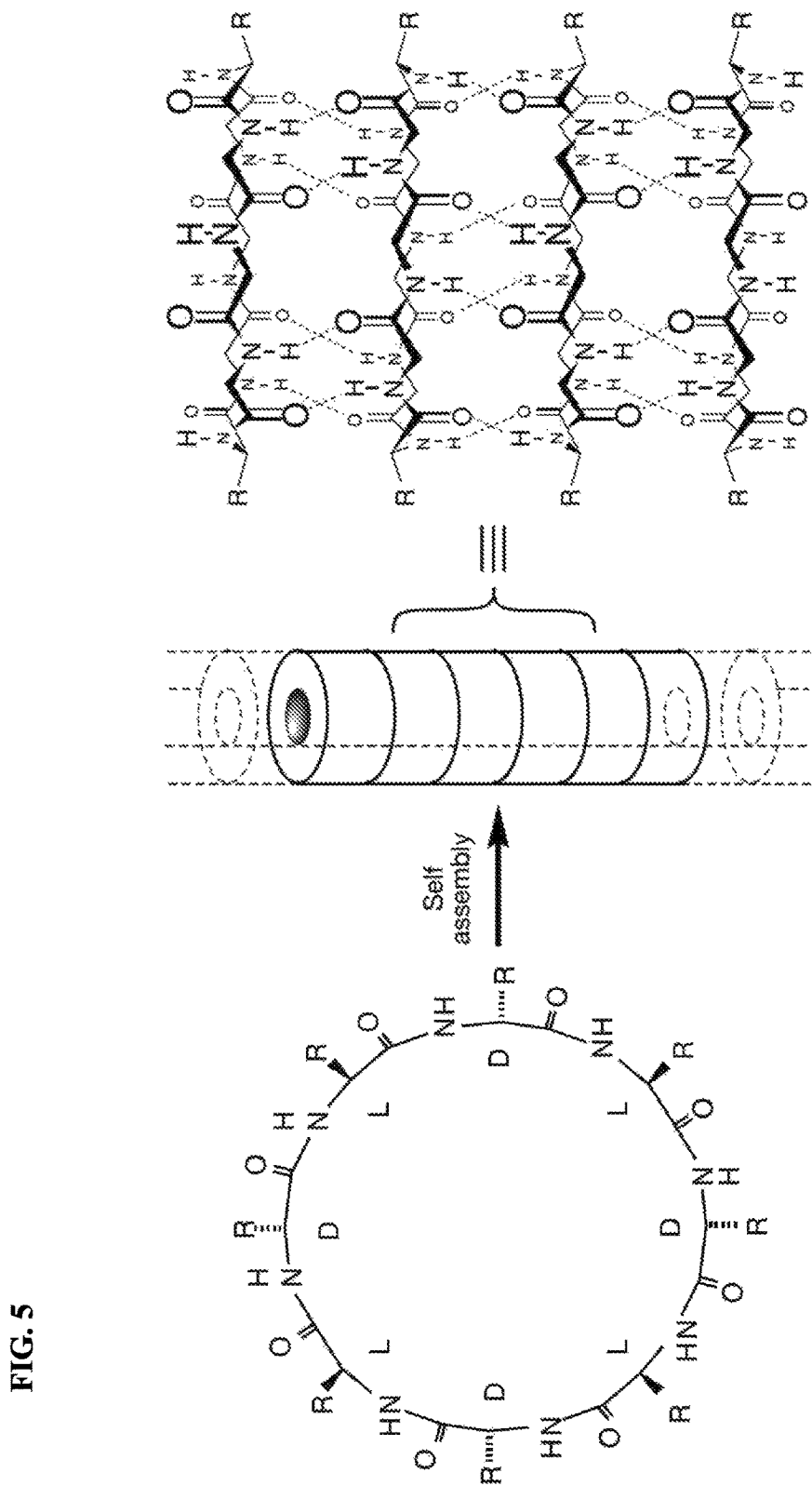
FIG. 5 shows a molecular structure of an embodiment of a DLCP nanotube, stabilized by intermolecular hydrogen bonding.

The cyclic peptide nanotubes can be formed by self-assembly of the cyclic peptides. As shown in FIG. 5, hydrogen bonding can provide the molecular stabilization for the nanotubes. As can be seen, the sidechains of alternating D and L (i.e., R and S) amino acid residues are entirely disposed on the exterior of the nanotube; the conformation taken by each cyclic peptide provides for interpeptide hydrogen bonding resulting in stacking of the cyclic peptides in a cylindrical array, with the amino acid residues disposed towards the external environment. In certain embodiments, the amino acids can be glutamine and leucine, alternating in each cyclic peptide to form a cyclic 8-mer containing four of each amino acid type. In other embodiments, other amino acids can be used, provided that the cyclic peptide forms comprising the amino acids can assume the proper conformation for stacking into the cylindrical nanotube array with sidechain directed towards the exterior of the cylinder.

The amino acids of alternating D and L (R and S) configuration can be the appropriate chiral form of amino acids such as those found in proteins (i.e., D and L forms of the ribosomal amino acids); alternatively, amino acids of structurals not found in proteins, or not found in nature, can be used. Amino acids having desirable sidechains can be prepared in enantiomerically pure form then assembled into the desired cyclic oligomer peptides. These cyclic forms can then self-assemble into the nanotubes. For example, cyclic peptides can possess sidechains available for functionalization, or for covalent cross-linking with a biocompatible polymer matrix, by appropriate selection of the amino acid residues used in formation of the cyclic peptide, as discussed in greater detail below.

Figure 6:
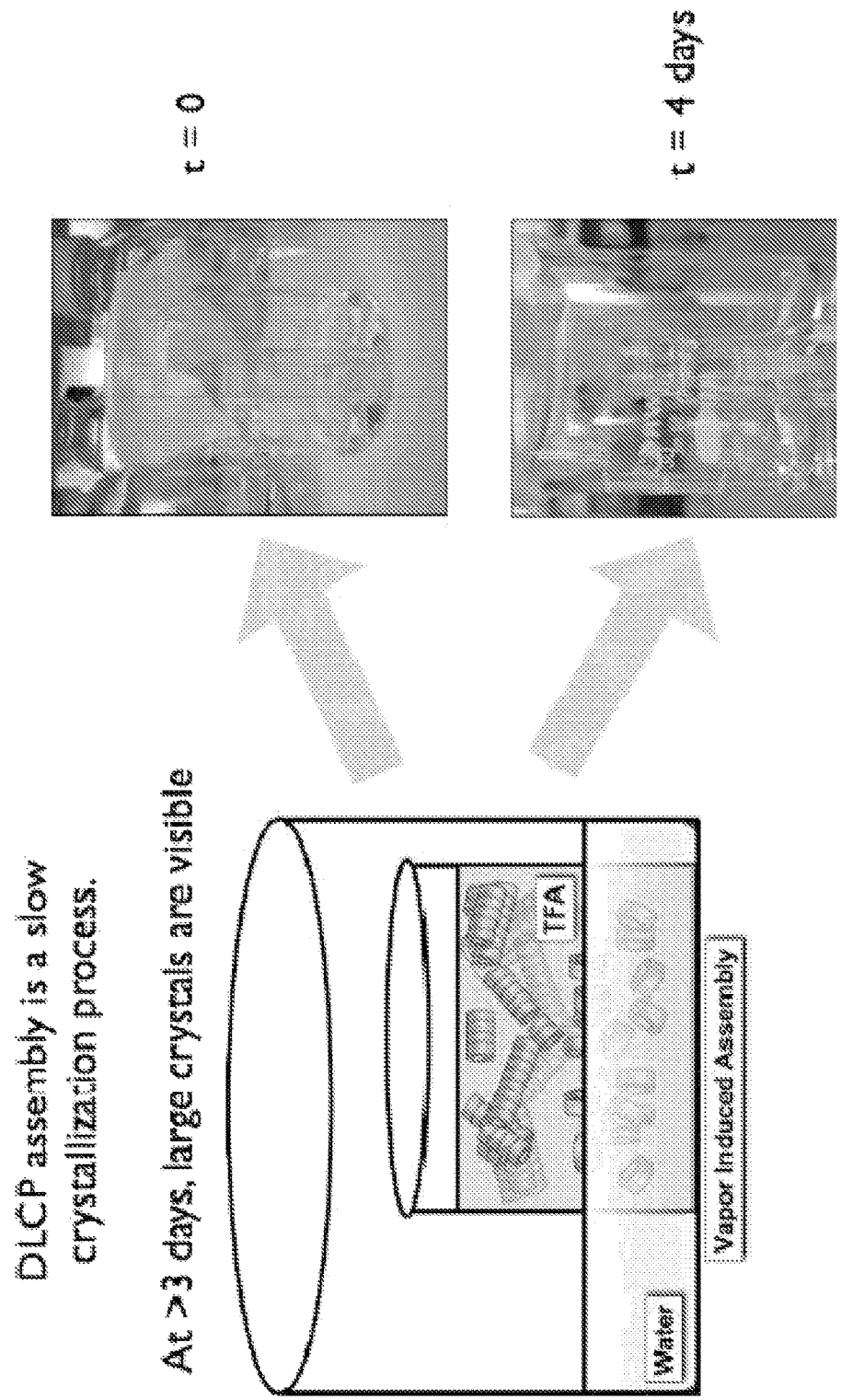
FIG. 6 shows a system used for preparation of the DLCP nanotubes by vapor equilibration self-assembly.

Nanotubes may be assembled using a variety of methods, including altering pH or ionic strength, altering temperature, changing solvent conditions, in response to specific soluble ions or molecules, or by nucleation at a solid-liquid or liquid-air interface. FIG. 6 shows one particular method for preparation of the nanotubes by self-assembly using vapor equilibration. A sample of the cyclic peptide oligomer selected for formation of the nanotubes is dissolved in trifluoracetic acid (TFA), then the TFA solution is placed in a container that allows vapor movement in and out. The open container is then disposed such that the TFA vapor can equilibrate with a separate open container of water, within an overall containment system to prevent complete evaporation instead of vapor equilibration. After several days, nanotubes self-assembled by the cyclic peptide oligomer, such as the glutamine-leucine (Q-L) cyclic 8-mer ("QL4") described above, can be recovered from the peptide solution. Alternatively, the nanotubes can be prepared as described in the Examples, below, by dissolving the cyclic peptide of which the nanotubes are to be composed in a solvent, e.g., trifluoracetic acid, then adding water and allowing the solution to stand for several days as the nanotubes form. They can be recovered using any of the well known techniques for separating a precipitate from a supernatant, e.g., centrifugation, filtration, and the like.

Figure 7:
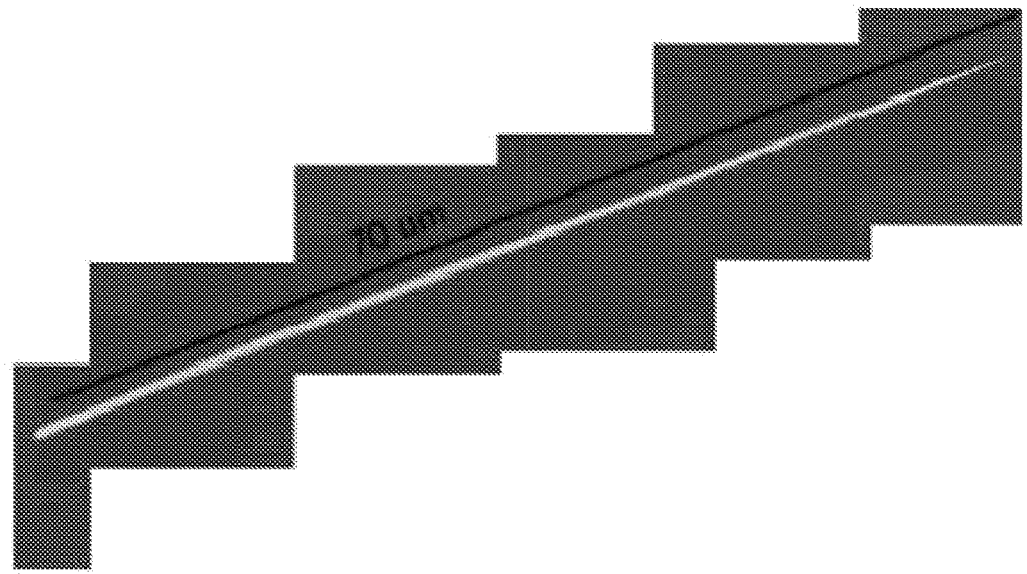
FIG. 7 is a microphotograph of a QL4 nanotube prepared by vapor equilibration self-assembly.
Figure 7:

FIG. 7 is a microphotograph of a QL4 nanotube prepared by the vapor equilibration method.

It is within ordinary skill to evaluate various cyclic peptides composed of amino acid residues of alternating absolute configuration (R and S, D and L), of various ring sizes (cyclic 6-mer, cyclic 8-mer, cyclic 10-mer, etc.) using the vapor equilibration self-assembly technique to evaluate the suitability of the particular cyclic peptide for nanotube formation and the properties of the nanotubes thus prepared.

Figure 8:
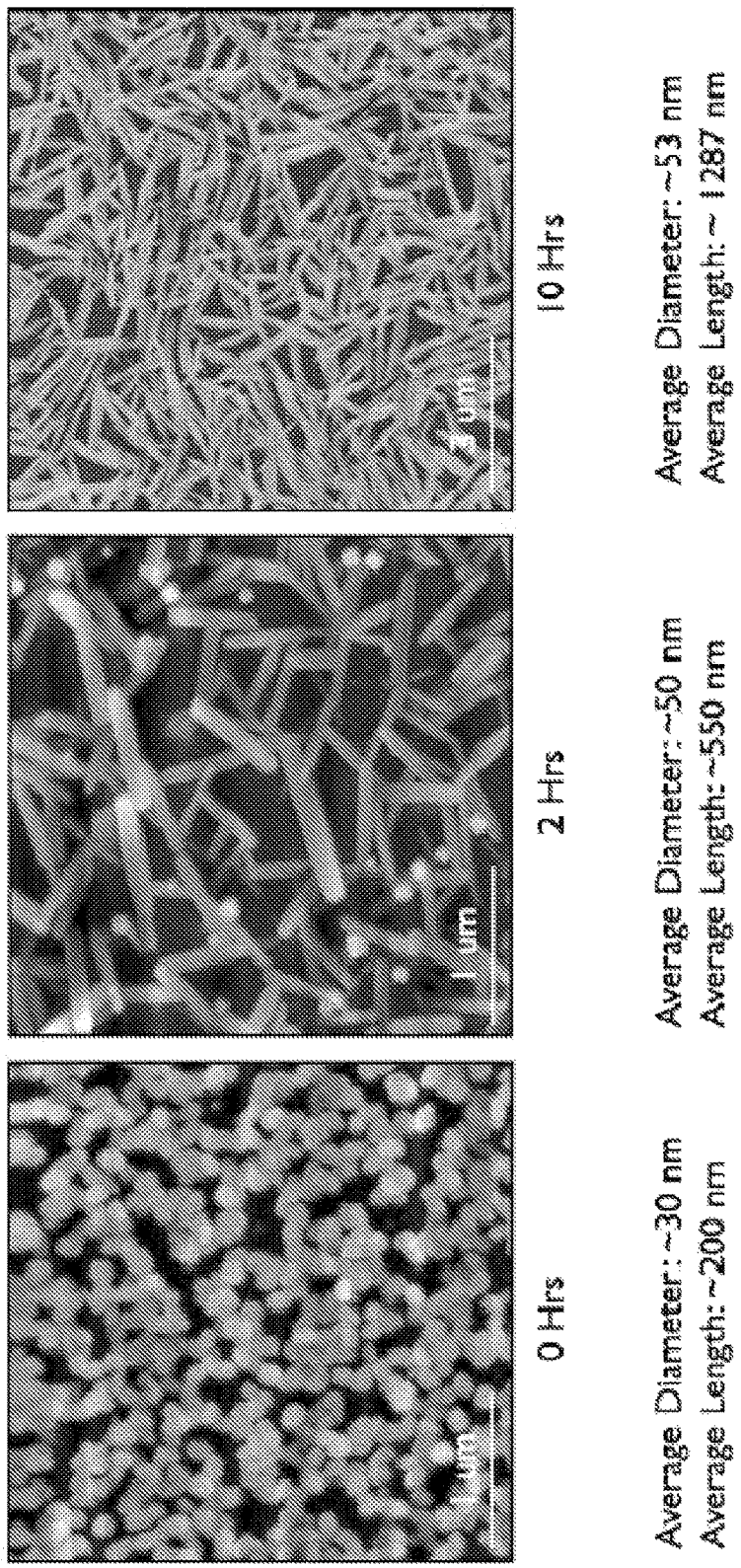
FIG. 8 is a series of microphotographs showing the time course of nanotube self-assembly using the vapor equilibration self-assembly technique.

The time dependence of nanotube self-assembly using the vapor equilibration method is illustrated in FIG. 8. As can be seen, nanotube morphology develops over a course of several hours. The most pronounced effect is elongation of the nanotubes; diameters in the system evaluated as shown in FIG. 8 had comparable nanotube diameters throughout, but by 10 hours the average nanotube entity had elongated from about 200 nm to about 1200 nm.

Figure 9:
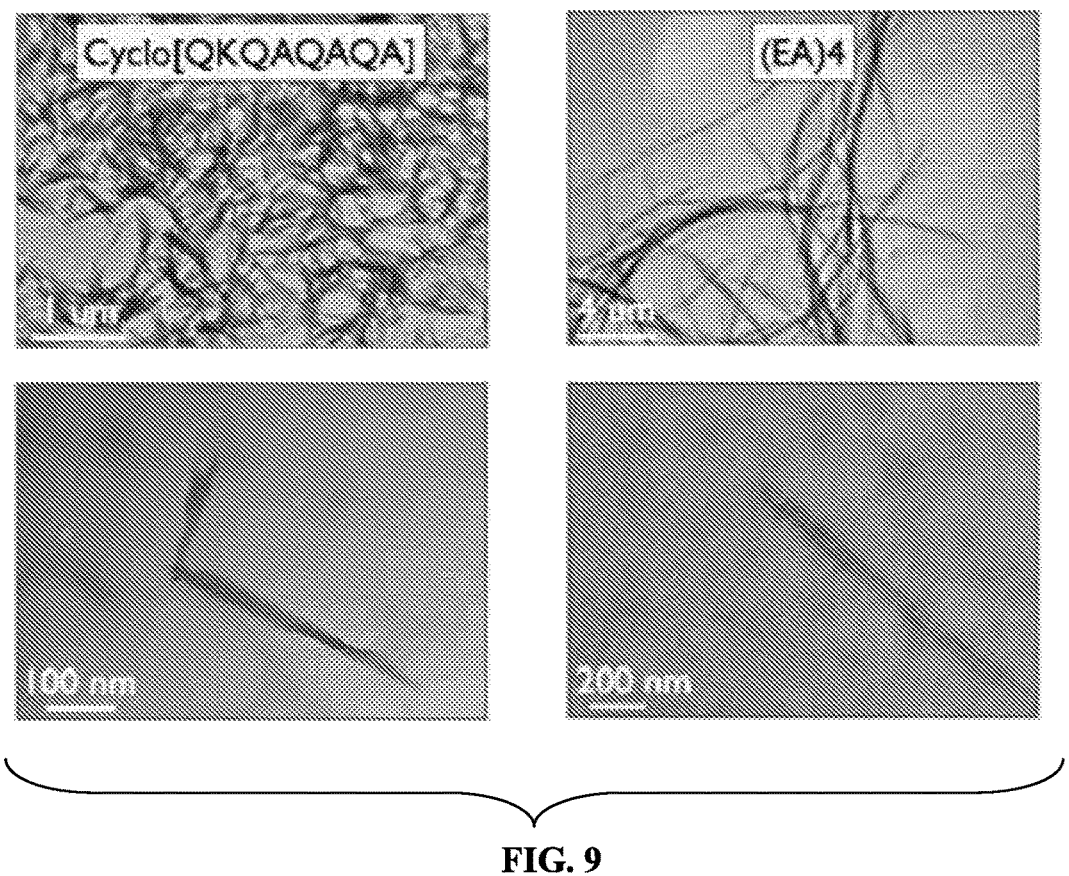
FIG. 9 is a series of microphotographs showing nanotube morphology of nanotubes prepared by vapor equilibration from QKQAQAQA versus (EA)$_4$ cyclic 8-mer peptides.

The morphology of the nanotubes obtained using the vapor equilibration process can be dependent upon the molecular composition of the cyclic peptide of which the particular nanotube is formed. For example, FIG. 9 shows a comparison of the morphology of nanotubes prepared from two different cyclic peptides under comparable conditions. The first column of two microphotographs show nanotubes self-assembled from the cyclic peptide cyclo (QKQAQAQA), i.e., a cyclic 8-mer peptide of sequence cyclo-(Gln-Lys-Gln-Ala-Gln-Ala-Gln-Ala); the second column of two microphotographs show nanotubes self-assembled from the cyclic peptide 8-mer $(EA)_4$, i.e., a cyclic 8-mer peptide of sequence cyclo-(Glu-Ala-Glu-Ala-Gly-Ala-Gly-Ala). In both cases the absolute configuration sequentially alternates between D and L (R and S) chiral forms of the respective amino acids.

Pre-assembled nanotubes can be combined with polymers, e.g., poly(caprolactone) (PCL), or poly(caprolactone)-gelatin mixtures, by fiber formation techniques well known in the art. Unassembled DLCPs may also be combined with polymers and assembled into nanotubes in situ, before or during the fiber formation process. Fiber formation techniques may include electrospinning or extrusion from a syringe or nozzle. Electrospinning is a technique that is well-known in the art, whereby a voltage applied across an extrusion nozzle and a collection surface induces the formation of fibers from a feeder solution. Extrusion can be performed starting with the combination of polymer and DLCPs dissolved in various solvents, or as a polymer melt consisting of pure polymer with dispersed nanotubes, and the fibers may be extruded into air or into a solvent bath. Post-processing may include drawing fibers by hand or with the help of a mechanical device, and drying.

Figure 10A:
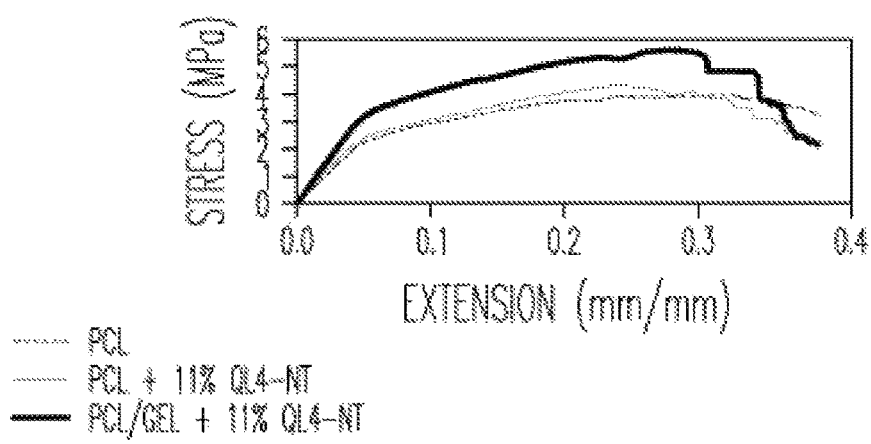
FIGS. 10A and 10B show graphic data showing the results of comparison of nanotube composite materials of the invention versus PCL lacking DLCP nanotube reinforcement.
Figure 10B:
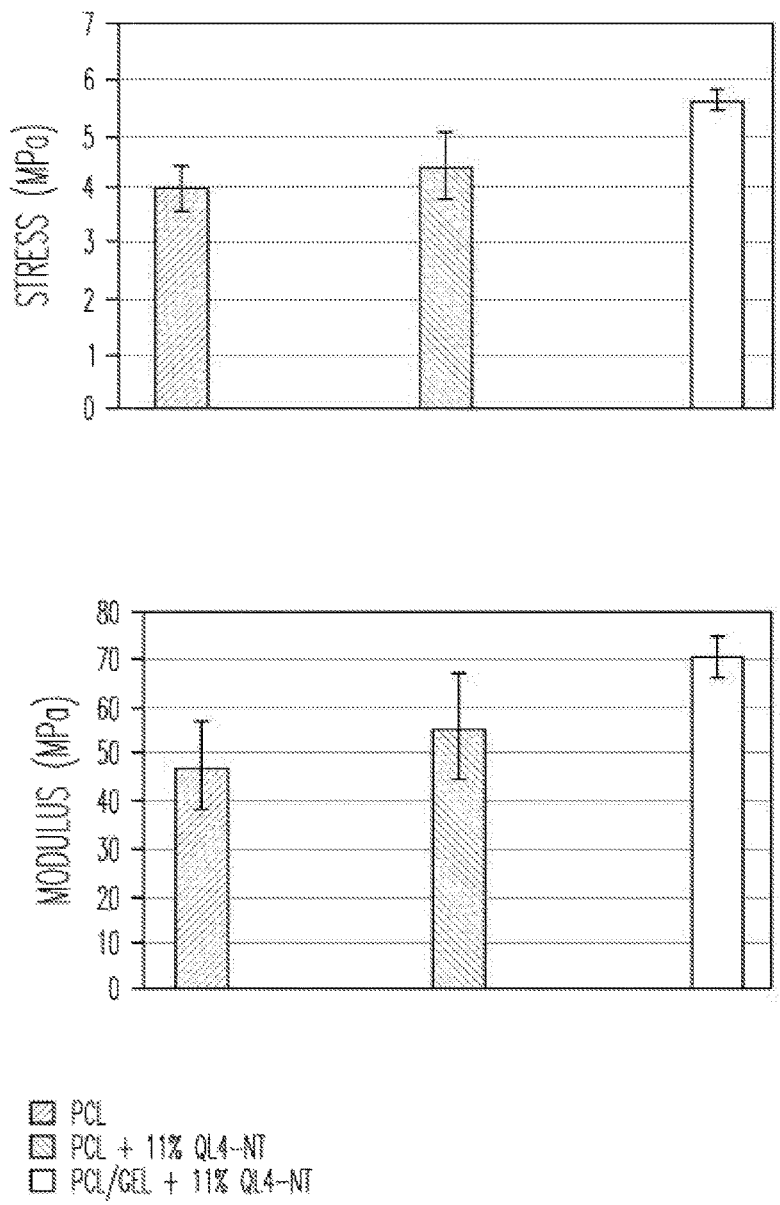

Comparison of nanotube-reinforced PCL composites and PCL samples lacking the nanotube reinforcement are shown in FIGS. 10A and 10B. FIGS. 10A and 10B show in two graphical formats the results of stretching versus force (mPa) for PCL fibers compared to PCL including 5.5% and 11% QL4 nanotubes. At the 11% nanotube reinforcement level, 40% higher strength and 50% higher Young's modulus were exhibited for the DLCP nanotube reinforced polymer composite material. A significant increase in physical strength is observed in the composite material of the invention relative to unreinforced samples of fiber composed of the same polymer PCL.

Figure 3A:
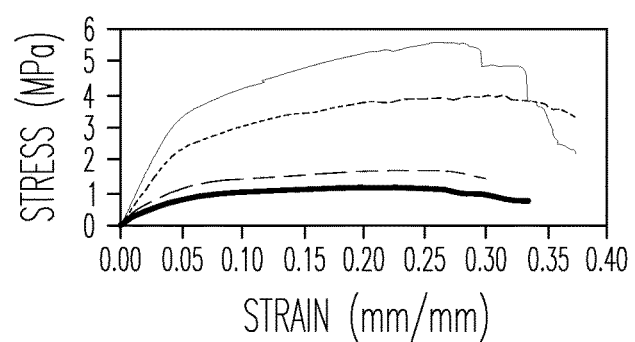
FIG. 3: (A) Characteristic stress-strain curve of PCL, reinforced PCL, PCL/gel, and reinforced PCL/gel (B) Ultimate tensile strength and Young's modulus of PCL, reinforced PCL, PCL/gel, and reinforced PCL/gel. Error bars represent 1 standard deviation. Sample sizes: PCL (n=4), PCL+11% DLCP-NT (n=2), PCL/Gel (n=3), PCL/Gel+11% DLCP-NT (n=3).
Figure 3B:
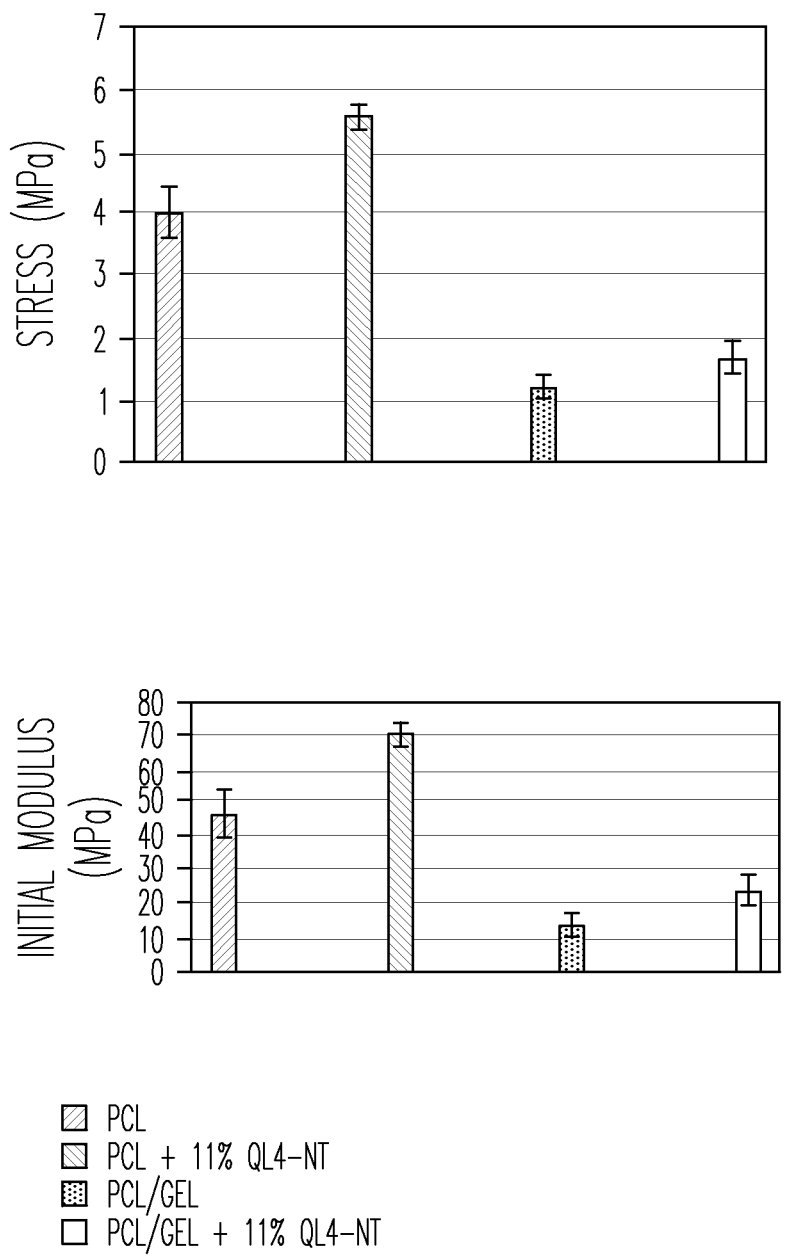

Further comparisons of the physical properties of nanotube-reinforced biocompatible polymer composite materials of the invention with art materials are shown in FIGS. 3A and 3B. In this study, a composition of the invention, PCL/gelatin fibers with DLCP nanotube reinforcement, compared to PCL/gelatin fibers alone, was examined for stress-strain and modulus data. The inventive composite of the invention displayed markedly enhanced physical properties.

Figure 11:
FIG. 11 shows an electron microphotograph of a nanotube prepared from a cyclic peptide comprising carboxylate sidechains, then treated with a heavy metal.

FIG. 11 shows an electron microphotograph of a nanotube prepared from a cyclic peptide comprising carboxylate sidechains, then treated with a heavy metal to show the periodicity of the cyclic peptide stacking. As can be seen, the carboxylate groups are disposed co-linearly with the axis of the nanotube.

FIG. 12 shows a force versus Displacement curves for indentation of composite fibers containing 0%, 1%, 4%, and 8% (weight-to-weight) of $(QL)_4$ nanotubes. Error bars represent one standard deviation (n=16). B. Young's Modulus versus weight percentage of $(QL)_4$ nanotube incorporation. Error bars represent one standard deviation (n=16). Elastic modulus measurements were made according to the procedure described below in the Examples.

Figure 13C:
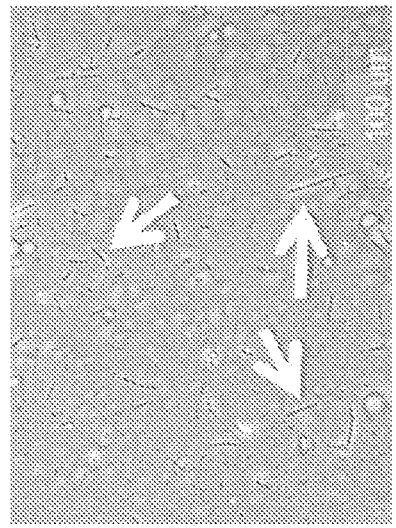
FIG. 13 shows (A) Photograph of (QL)$_4$, PDLLA composite mesh. (B) Electron micrograph of composite nanofibers. (C) Optical micrograph of (QL)$_4$ nanotubes after solvent extraction from fibers.
Figure 13B:
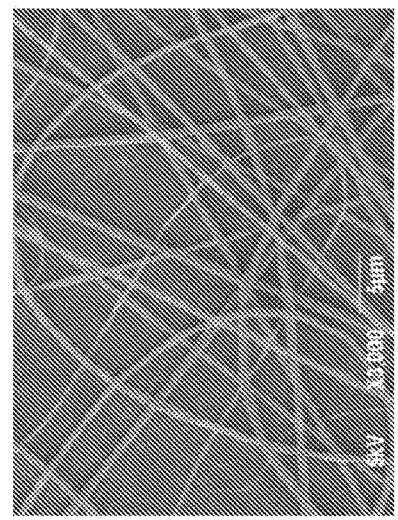
Figure 13A:
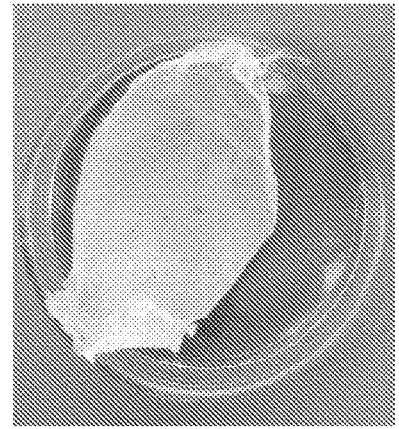

FIG. 13(A) shows a normal perspective photograph of a composite mesh of $(QL)_4$ in PDLLA. As can be seen, the mesh can form a coherent structure. FIG. 13(B) shows an electron micrograph of composite nanofibers. The reinforcing DLCP fibers can be seen to be continuous in the matrix. FIG. 13(C) show an optical micrograph of $(QL)_4$ nanotubes after solvent extraction from fibers. This indicates that the nanotubes remain intact within the fiber. The arrows indicate intact DLCP fiber segments that have been extracted from the DLCP-PDLLA matrix.

Other applications in tissue engineering can make use of the DLCP nanotube reinforced polymer composite materials of the invention. For instance, the materials can be used in the forms of fibers, thin films, or injection-molded bulk objects of various shapes. For example, synthetic vertebral discs can be produced by techniques such as injection molding, wherein the enhanced physical properties of strength and modulus are advantageous in providing synthetic vertebral disc replacements of exceptional strength and durability. Synthetic fibers and films can be useful in the repair of ligaments and tendons, such as in reattachment of torn musculature to their bone anchor points. Thus, materials such as spinal fusion cages, load-bearing fibrous tissue engineering structures, and shape-memory materials can be prepared using the inventive composite materials.

The potential applications of this reinforcing technology are broad. As DLCPs are both biocompatible and biodegradable, they are suitable for in vivo use within synthetic biostructures, as well as reinforcement within environmentally sustainable materials. Under the umbrella of synthetic biostructures the technology is applicable to synthetic load-bearing tissues including ligaments, tendons, cartilage and bones, as well as sutures and wound dressings. In each of these cases, the current materials suffer from a lack of mechanical strength, acidic decomposition products, and fixed degradation kinetics. By incorporating a DLCP nanotube reinforcement of the appropriate size and chemistry, the material can be reinforced, buffered upon decomposition, and influenced to degrade over longer or shorter time-scales.

For example, the DLCP-PDLLA composite can be used as a stiffer replacement for PDLLA spinal fusion cage. The stiffness (elastic modulus) of the fibers at the single nano-fiber level have been studied using an atomic-force microscope based nano-indentation technique.

Spinal Fusion Cages

Chronic back pain is a major unmet medical need. One common method for alleviating the symptoms is to fuse two or more vertebrae of the spine together, decreasing pain but also decreasing mobility across the damaged area. The current methods used to fuse vertebrae employ titanium screws and plates that secure the vertebrae, or spinal fusion cages that sit between the vertebrae, influencing the body to grow bone and fuse the two vertebrae naturally. Unfortunately, in both cases, the metal remains in the body and can lead to downstream complications. Because of this, investigators have moved towards polymer based spinal fusion cages that are biodegrade. The first iteration of these devices was based on crystalline poly-L-lactic acid (PLLA). However, as the polymer breaks down, it leaves irritating crystallites behind that cause inflammation in the area. The next iteration used amorphous, poly-D,L-lactic acid (PDLLA). While PDLLA leaves no crystallites behind, it also suffers from a lack of rigidity. Specifically, under a fixed stress, the material will fail over time. This process is described in the citations below. In our future work, we aim to stabilize these PDLLA spinal fusion cages with DLCP nanotubes, preventing this fixed-stress weakness.

See, for example:

Engels et al. Time-dependent failure of amorphous polylactides in static loading conditions. Journal of Materials Science: Materials in Medicine (2010) vol. 21 (1) pp. 89-97

Smit et al. Time-dependent failure in load-bearing polymers: a potential hazard in structural applications of polylactides. Journal of Materials Science: Materials in Medicine (2010) vol. 21 (3) pp. 871-878.

Within the field of environmentally sustainable materials, we believe that improvement of biodegradable plastics to be the main target application. Biodegradable plastics often suffer from poor mechanical strength and reinforcement with a bio-friendly component is necessary. As DLCPs are composed of natural amino acids, they will degrade over relatively short timeframes and have the potential to nourish the ecosystem in which they are disposed.

EXAMPLES

D,L-Cyclic Peptide Nanotube Assembly

D,L-cyclic peptides ([QL]$_4$) were mixed with 100% trifluoroacetic acid (TFA) at a concentration of 1.25-5 mgs/ml in a glass scintillation vial. Once dissolved, pure water was added drop-wise until the total volume-to-volume percentage of water-to-TFA was 40%. The vial was capped and left to sit, undisturbed for 3-5 days. Peptide nanotubes were separated by centrifugation.

Nanomechanical Analysis by AFM-Based Indentation:

Indentation studies were carried out on an atomic force microscope, outfitted for mechanical analysis. A spherical glass bead was attached to a tipless cantilever and was pressed into individual fibers. The resultant data was used to plot the force-displacement graphs presented in FIG. 12. Modulus was calculated by assuming a Hertzian contact model—an elliptical cross-sectional contact area that is created by two intersecting cylinders of disparate radii. This approximation holds true due to the large diameter of the bead (40 um) and the single fiber (800 nm). The elastic modulus of PDLLA increased 2-to-4-fold depending on the weight percentage of peptide nanotube within the polymer. See, for example:

Han, et al. Geometrically-controlled mechanically responsible polyelectrolyte tube arrays. *Advanced materials* (2011), 23, 4667-4673.

All patents and publications referred to herein are incorporated by reference herein to the same extent as if each individual publication was specifically and individually indicated to be incorporated by reference in its entirety.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A nanotube-reinforced polymer composite, comprising a plurality of nanotubes within a polymer matrix,
   wherein each nanotube comprises a self-assembling, non-covalently bonded plurality of D,L cyclic peptide molecules,
   wherein each D,L cyclic peptide molecule is a cyclic oligomer of about 6-12 α-amino acid residues, wherein each amino acid residue bears an α-hydrogen atom and a non-hydrogen α-substituent,
   wherein the amino acid residues of each cyclic peptide molecule have alternating absolute configurations,
   and wherein the amino acid residues of each D,L cyclic peptide molecule comprise a first type of amino acid of a first absolute configuration, and a second type of amino acid of an opposite absolute configuration.

2. The composite of claim 1, wherein the nanotubes are aligned with each other within the polymer matrix.

3. The composite of claim 1, wherein the nanotubes are substantially randomly disposed within the polymer matrix.

4. The composite of claim 1, wherein the polymer matrix comprises one or more biocompatible polymers.

5. The composite of claim 1, wherein the polymer matrix comprises a polymer selected from the group consisting of a poly(caprolactone), a poly(caprolactone)/gelatin blend, a poly(lactide), a poly(glycolide), a poly(lactide-glycolide), a poly-D,L-lactic acid chitosan, hyaluronic acid, cellulose, alginate, silk, or any combination thereof.

6. The composite of claim 1, wherein the first type of amino acid is glutamine and the second type of amino acid is leucine, wherein the glutamine and the leucine are of opposite absolute configuration; or wherein the first type of amino acid is glutamate and the second type of amino acid is alanine, wherein the glutamate and the alanine are of opposite absolute configuration.

7. The composite of claim 1, further comprising a third type of amino acid, wherein the third type of amino acid substitutes in the cyclic peptide for an amino acid residue of the same absolute configuration.

8. The composite of claim 1, wherein the D,L cyclic peptide molecule comprises amino acids bearing functionalized sidechains for subsequent interaction with a derivatizing material.

9. The composite of claim 8, wherein the functionalized sidechains are adapted for interaction with a target body tissue substrate for tissue repair.

10. The composite of claim 9, wherein the target body tissue substrate comprises bone, tendon, ligament, or cartilage.

11. A synthetic biostructure comprising the composite of claim 1.

12. The synthetic biostructure of claim 11, wherein the synthetic biostructure is a fiber, a stent, a suture, a wound dressing, a spinal fusion cage, a bone screw or plate, or a synthetic ligament, tendon, cartilage, or bone material.

13. The synthetic biostructure of claim 12, wherein the synthetic biostructure is a fiber, and wherein the fiber is prepared by electrospinning of the polymer comprising the plurality of nanotubes therein.

14. The synthetic biostructure of claim 12, wherein the synthetic biostructure is a fiber, and wherein the plurality of nanotubes are aligned parallel to the length of the fiber.

15. The synthetic biostructure of claim 11, comprising a mat comprising a plurality of aligned or non-aligned fibers.

16. The synthetic biostructure of claim 11, comprising an injection-molded polymer comprising the plurality of nanotubes therein.

17. The synthetic biostructure of claim 16, injection molded into a spinal fusion cage or a bone screw or plate.

18. A method of preparing the composite of claim 1, comprising, first preparing self-assembled nanotubes from D,L cyclic peptide molecules, then, incorporating the nanotubes into the polymer matrix.

19. The method of claim 18, wherein the nanotubes are prepared by precipitation from a solvent by a non-solvent.

20. The method of claim 19, wherein the solvent is trifluoracetic acid and the non-solvent is water, or wherein the polymer matrix is poly(caprolactone), a poly(caprolactone)-gelatin blend, poly(lactide-glycolide) or poly-D,L-lactic acid, or any combination thereof, or both.

21. A method of repairing a damaged ligament, tendon, cartilage, or bone, comprising use of a composite of claim 1, or a synthetic biostructure of claim 11, to fill, reinforce, or to connect the ligament, tendon, cartilage or bone to a substrate.

22. A method of repairing a damaged spinal column, comprising disposing the spinal fusion cage of claim 12 around a section of spinal column of a patient in need thereof.

23. A nanotube-reinforced polymer composite, comprising a plurality of nanotubes within a polymer matrix,
wherein each nanotube comprises a self-assembling plurality of D,L cyclic peptide molecules bonded together only by inter-peptide hydrogen bonding,
wherein each D,L cyclic peptide molecule is a cyclic oligomer of about 6-12 α-amino acid residues each bearing an α-hydrogen atom and a non-hydrogen α-substituent,
wherein the amino acid residues of each cyclic peptide molecule have alternating absolute configurations,
and wherein the amino acid residues of each cyclic peptide molecule include a first type of amino acid of a first absolute configuration, and a second type of amino acid of an opposite absolute configuration.

* * * * *